United States Patent [19]

Noack

[11] Patent Number: Plant 7,282

[45] Date of Patent: Jul. 31, 1990

[54] GROUNDCOVER ROSE PLANT NAMED 'FLOWER CARPET'

[75] Inventor: Werner Noack, Guetersloh, Fed. Rep. of Germany

[73] Assignee: Pan-Am Northwest, Inc., Surrey, Canada

[21] Appl. No.: 346,393

[22] Filed: May 2, 1989

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Christie, Parker & Hale

[57] ABSTRACT

A new and unusual groundcover rose bearing deep pink blooms.

2 Drawing Sheets

BACKGROUND OF THE INVENTION

Groundcover rose plants have been known which have been usefully included in various landscaping plans. However, there is always a place for new varieties of groundcover roses, especially varieties which have desireable groundcover-type growth habit, produce attractive flowers and are resistent to disease.

SUMMARY OF THE INVENTION

The present invention relates to a new and distinct variety of groundcover rose plant bearing miniature blooms, which was originated by my crossing as seed parent the variety known as "Immensee" and as pollen parent the variety known as "Amanda". The varietal denomination of this new rose is "Flower Carpet".

Among the novel characteristics possessed by this new variety which distinguish it from its parents and all other varieties of which I am aware are its effective groundcover-type habit of growth, attractive deep pink decorative miniature blooms and resistance to disease. This new groundcover plant grows and covers well, and produces lovely pink deep flowers that open reliably and remain attractive upon aging.

Asexual reproduction by propagation by cuttings of the new variety as performed in British Columbia, Canada shows that the foregoing and other distinguishing characteristics come true to form and are established and transmitted through succeeding propagations.

BRIEF DESCRIPTION OF THE DRAWINGS

The accompanying drawings show typical specimens of the vegetative growth and flowers of the new variety in different stages of development and depicted in color as nearly true as it is reasonably possible to make the same in a color illustration of this character.

DETAILED DESCRIPTION OF THE PREFERRED EMBODIMENTS

The following is a detailed description of my new variety, with color terminology in accordance with The Royal Horticultural Society Colour Chart (RHSCC). The terminology used in color description herein refers to plate numbers in the aforementioned color chart, e.g., "67B" is plate 67B of The Royal Horticultural Society Colour Chart.

Parentage: Seedling.

*Seed parent.*—"Immensee".

*Pollen parent.*—"Amanda".

Class: Groundcover.

The following observations are made of specimens grown outdoors in British Columbia, Canada, during the month of July.

FLOWER

Blooming habit: Continuous.

A. Bud:

(1) *Size.*—Small.

(2) *Form.*—Rounded.

(3) *Color.*—As sepals divide, bud color is deep pink, near 67B to 67A.

(4) *Sepals.*—Longer than bud, pointed.

(5) *Penduncle.*—Length — short. Aspect — crooked. Strength — strong for a groundcover. Color — Light green.

Bloom:

(1) *Size.*—Average size when fully expanded — about $1\frac{3}{4}$ inches.

(2) *Borne.*—In large sprays.

(3) *Form.*—Cupped at first, becoming flat.

(4) *Petalage.*—Number of petals under normal conditions — about 15.

(5) *Color.*—After sepals fall and petals unfurl, predominant flower color viewing petals' top surface is near 67B to 67A, color of petal undersurface is slightly lighter toned. As flower opens, near white center becomes visible due to near white coloring of petals toward point of petal attachment. Also visibly evident is the yellow coloring of pollen and reproductive organs which contrast attractively with the near white petal coloring approaching the point of attachment and the predominant deep pink petal coloring, near 67B to 67C. As flowers age, color lightens to near 67D with somewhat more pronounded color grading (lightening) toward flower centers.

C. Petals:

(1) *Texture.*—Medium.

(2) *Appearance.*—Inside satiny and outside satiny.

(3) *Form.*—Broad, fan shaped, some outer petals with indented central margin.

(4) *Arrangement.*—Regularly arranged, imbricated.

(5) *Petaloids in center.*—Few.

(6) *Persistence.*—Drop off cleanly.

(7) *Fragrance.*—None.
(8) *Lasting quality.*—Long lasting quality on plant.

REPRODUCTIVE ORGANS

A. Stamens, filaments and anthers:
*Arrangement and color.*—Regularly arranged around styles. Color — filaments nearly transparent.
B. Pollen:
*Color.*—Yellow.
C. Styles: Even length, bunched, thin.
Stigmas:
*Color.*—Yellow.
Hips: Round, small, green with reddish tint.

PLANT

A. Form: Compact, spreading, ideal groundcover growth habit.
B. Growth: Vigorous and rambling.
*Height attained.*—About 20 inches.
C. Foliage: Compound 7 to 9 leaflets.
(1) *Size.*—Small.
(2) *Quantity.*—Very abundant.
(3) *Color.*—New foliage: Upper side — reddish purple-green. Under side — slightly lighter than upper side. Old foliage: Upper side — near 141B. Under side — near 141D.
(4) *Shape.*—Oval, pointed.

(5) *Texture.*—Upper side is leathery and glossy; under side is matte.
(6) *Edge.*—Serrate.
(7) *Serration.*—Ordinary.
(8) *Leaf stem.*—Color — light green with reddish overlay.
(9) *Stipules.*—Light green.
(10) *Resistance to disease.*—Blackspot — Excellent. Mildew — Excellent. Rust — Excellent.
D. Wood:
(1) *New wood.*—Color — light green. Bark — smooth.
(2) *Old wood.*—Color — medium green. Bark — smooth.
E. Thorns:
(1) *Thorns.*—Quantity (main stalk) — average. On laterals from stalk — average. Form — long, slightly curved downward. Length — medium. Color — pinkish tan. Position — irregular.
(2) *Prickles.*—None.
F. Winter hardiness: Winter hardy.

I claim:

1. A new and distinct variety of groundcover rose plant, substantially as shown and described, characterized particularly by low, spreading, dense growth habit and deep pink flowers.

* * * * *

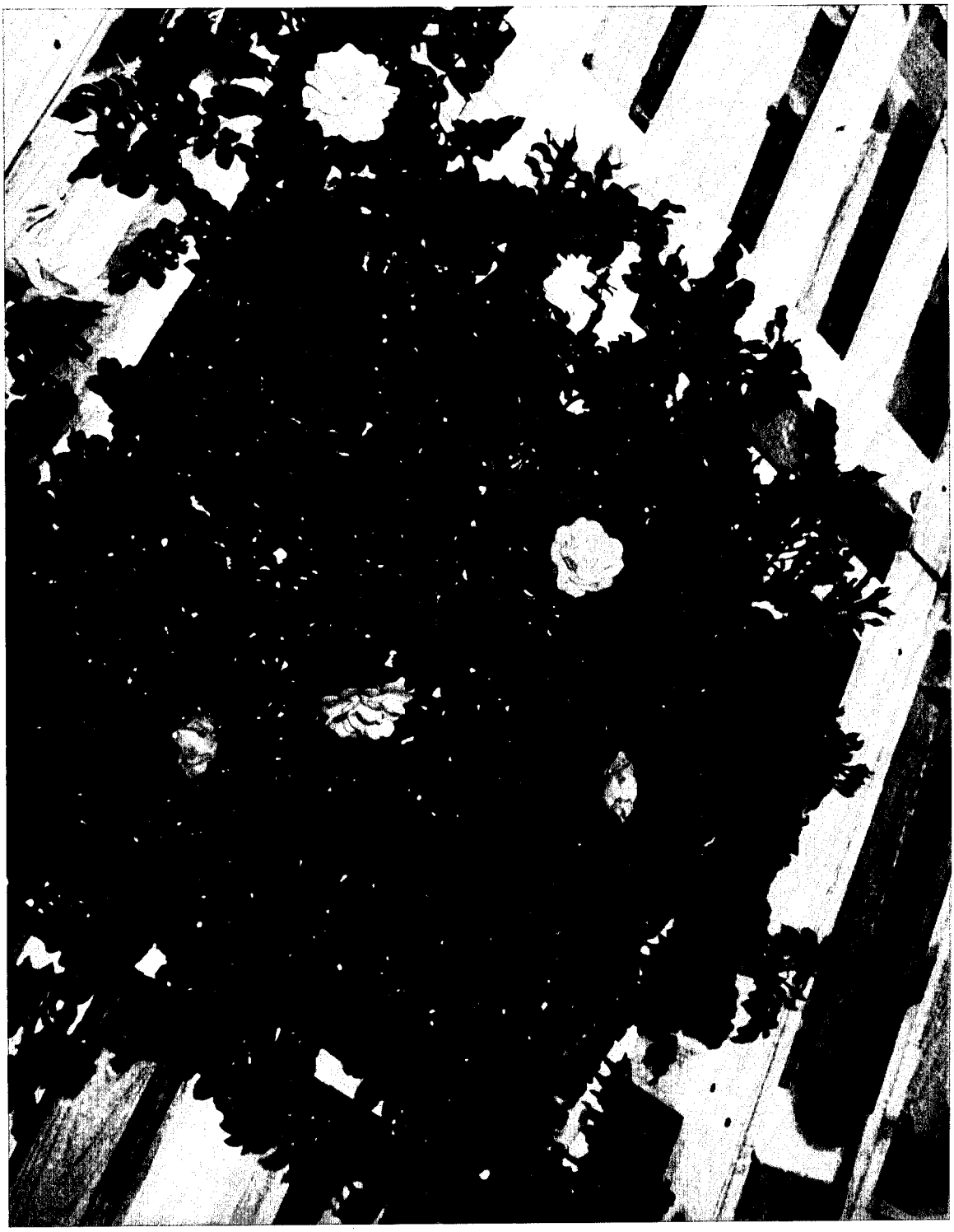

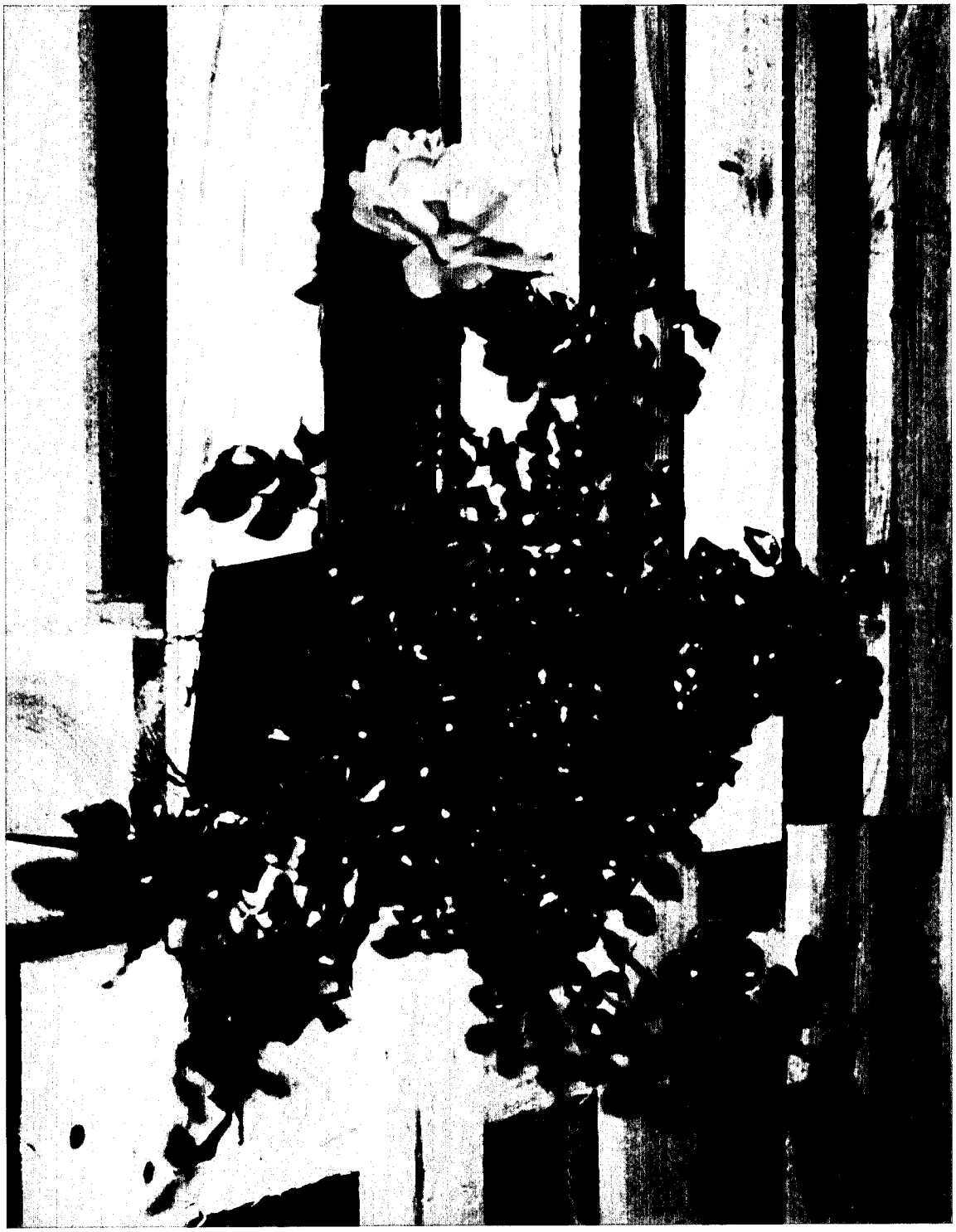

UNITED STATES PATENT AND TRADEMARK OFFICE

CERTIFICATE OF CORRECTION

PATENT NO. : PP 07,282
DATED : July 31, 1990
INVENTOR(S) : Noack

It is certified that error appears in the above-identified patent and that said Letters Patent is hereby corrected as shown below:

Title page,
Item [54], Title, delete "'FLOWER CARPET'" and insert -- NOATRAUM --.

Column 1,
Line 16, delete "FLOWER CARPET" and insert -- NOATRAUM --.

Signed and Sealed this

Twenty-eighth Day of February, 2006

JON W. DUDAS
*Director of the United States Patent and Trademark Office*